(12) United States Patent
Otsubo et al.

(10) Patent No.: US 7,744,577 B2
(45) Date of Patent: Jun. 29, 2010

(54) DISPOSABLE PULL-ON WEARING ARTICLE

(75) Inventors: Toshifumi Otsubo, Kagawa-ken (JP);
Naoto Ohashi, Kagawa-ken (JP);
Yusuke Kawakami, Kagawa-ken (JP);
Makoto Ichikawa, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 589 days.

(21) Appl. No.: 11/423,967

(22) Filed: Jun. 14, 2006

(65) Prior Publication Data

US 2006/0282058 A1 Dec. 14, 2006

(30) Foreign Application Priority Data

Jun. 14, 2005 (JP) ............... 2005-173997

(51) Int. Cl.
*A61F 13/15* (2006.01)
*A61F 13/20* (2006.01)

(52) U.S. Cl. ............... 604/385.22; 604/385.01; 604/385.03; 604/385.11; 604/386; 604/387; 604/389; 604/391; 604/392

(58) Field of Classification Search ........... 604/385.01, 604/385.03, 385.11, 386, 387, 389, 391, 604/392, 385.22
See application file for complete search history.

(56) References Cited

U.S. PATENT DOCUMENTS

| | | | | |
|---|---|---|---|---|
| 5,074,854 A | * | 12/1991 | Davis | 604/385.11 |
| 5,624,428 A | * | 4/1997 | Sauer | 604/391 |
| 5,830,206 A | * | 11/1998 | Larsson | 604/390 |
| 6,210,388 B1 | * | 4/2001 | Widlund et al. | 604/390 |
| 6,508,797 B1 | * | 1/2003 | Pozniak et al. | 604/385.11 |
| 6,579,275 B1 | * | 6/2003 | Pozniak et al. | 604/390 |
| 6,972,012 B1 | * | 12/2005 | Pozniak et al. | 604/386 |
| 7,497,852 B2 | * | 3/2009 | Kawakami | 604/391 |
| 2003/0216706 A1 | * | 11/2003 | Olsson et al. | 604/387 |
| 2004/0019343 A1 | * | 1/2004 | Olson et al. | 604/385.24 |
| 2006/0004341 A1 | * | 1/2006 | Olson et al. | 604/385.22 |
| 2006/0089616 A1 | * | 4/2006 | Belau et al. | 604/389 |

FOREIGN PATENT DOCUMENTS

JP 1-141711 9/1989

(Continued)

OTHER PUBLICATIONS

Written Opinion for PCT/JP2006/311799, dated Dec. 17, 2007.*

*Primary Examiner*—Tatyana Zalukaeva
*Assistant Examiner*—Ginger T Chapman
(74) *Attorney, Agent, or Firm*—Lowe Hauptman Ham & Berner LLP

(57) ABSTRACT

A disposable pull-on wearing article has its waist region divided into a front section and a rear section and connector sheets 21 adapted to connect these two sections together. Each of the connector sheets has joint zones to be joined to the front section and the rear section, respectively, and a non-joint zone interposed between the joint zones so as to define a tear-apart line extending in vertical direction along which the article is torn apart. The non-joint zone has a tensile strength of at least 8N in the waist-surrounding direction and a tear strength in a range of 0.1 to 12N also in the waist-surrounding direction.

18 Claims, 11 Drawing Sheets

FOREIGN PATENT DOCUMENTS

| | | |
|---|---|---|
| JP | 4-371147 | 12/1992 |
| JP | 5-317356 | 12/1993 |
| JP | 8-507699 | 8/1996 |
| JP | 2002-153509 | 5/2002 |
| JP | P3421030 | 4/2003 |
| WO | 97/13485 | 4/1997 |
| WO | 2005/016214 | 2/2005 |
| WO | WO 2006/134895 A1 * | 12/2006 |

* cited by examiner test condition
size of test piece   width 25mm × length 100mm
inter-chuck distance   50mm
clamp margin   25mm
stress rate   200mm/min test condition
inter-chuck distance   100mm
clamp margin   25mm
stress rate   200mm/min

DISPOSABLE PULL-ON WEARING ARTICLE

BACKGROUND OF THE INVENTION

The present invention relates to a disposable pull-on wearing article such as a disposable pull-on diaper or training pants.

Conventionally, disposable pull-on diapers are well known in the form of a disposable pull-on wearing article. In one example of well known pull-on diapers, a front waist region and a rear waist region are joined together along transversely opposite side edges thereof and these side edges may be torn apart to take the diaper off from the wearer's body. For example, Japanese Unexamined Patent Application Publication No. 1992-371146 (hereinafter referred to "REFERENCE 1") discloses a disposable pant which can be used as the disposable pull-on diaper. In the case of the pant disclosed therein, a front waist region and a rear waist region are joined together along transversely opposite side edges thereof by use of a heat-sealing means. These side edges joined together in this manner have an appropriate strength such that the pant can be easily torn apart along these side edges to take the pant off from the wearer's body. In the pant, the front waist region and the rear waist region are respectively provided with a plurality of thread-like elastic members extending in the transverse direction of these waist regions and attached in a stretched state thereto while the crotch region is provided with a plurality of thread-like elastic members attached in a stretched state thereto so as extend along the peripheral edges of the respective leg-holes.

There has already been proposed also a pull-on wearing article including panels which are elastically stretchable in the direction of the waist line and interposed between a front waist region and a rear waist region. For example, National Publication of Translated Version No. 1996-507699 (hereinafter referred to "REFERENCE 2") discloses a disposable pull-on diaper comprising an absorbent "chassis" and a pair of elastically stretchable "panels". This diaper further comprises a waist-hole and a pair of the leg-holes. The "panels" which are elastically stretchable in the direction of the waist line are respectively provided in the vicinity of transversely opposite lateral regions of the wearer and attached to the "chassis" along predetermined joint lines. With this diaper put on the wearer's body, the "chassis" covers the front and rear waist regions as well as the crotch region of the wearer while the "panels" are elastically stretchable and contractible to make the diaper fit the lateral regions of the wearer's waist. When the diaper put on the wearer's body has been soiled with bodily discharges, the "panels" may be torn off from the "chassis" along the joint lines to take the diaper off from the wearer's body without the anxiety that the wearer's body might be soiled with bodily discharges.

The disposable diaper disclosed in Japanese Unexamined Patent Application Publication No. 1993-317356 (hereinafter referred to "REFERENCE 3") is of pull-on type and a front waist region is provided along transversely opposite side edges with tear-apart lines used to tear the front waist region apart from a rear waist region. These tear-apart lines are in the form of intermittent slits or perforations (referred to as perforated lines) and extend in the vertical direction of the diaper across waist-surrounding elastic member and leg-surrounding elastic members. The diaper soiled with bodily discharges can be taken off from the wearer's body without anxiety that the wearer's body might be soiled with bodily discharges by tearing the front waist region apart from the rear waist region along the respective tear-apart lines.

Japanese Patent Publication No. 3421030 (hereinafter referred to "REFERENCE 4") discloses a disposable undergarment provided with a tear-apart panel. The tear-apart panel defines a zone in which a front section and a rear section of the disposable undergarment can be torn apart from each other and continuously extends from one of the leg-holes to the waist-hole. The tear-apart panel comprises a strip of nonwoven material having no locally weakened part along which the strip can be easily torn apart with the bare hands. Preferably, this tear-apart panel has a transverse tensile strength in a range of 196.85 g/cm to 1968.50 g/cm, more preferably in a range of 787.40 g/cm to 1181.10 g/cm. According to an embodiment illustrated in this document, the tear-apart panel is adapted to connect the front section and the rear section of the undergarment and has its outer surface joined to respective outer surfaces of the front section and the rear section of the undergarment.

In the case of the pant disclosed in REFERENCE 1, each side edge of the front and rear waist regions comprises an inner sheet formed from a nonwoven fabric and an outer sheet formed from a lamination of plastic film and nonwoven fabric or the like. Assumed that the side edges of the front waist region each comprising a plurality of the sheet material layers are placed upon and joined to the side edges of the rear waist region by a heat-sealing means each of the side edges of the pant would comprise four to six sheet material layers heat sealed together. An effort to tear these side edges joined together apart one from another to take the pant off from the wearer's body may sometimes peel the nonwoven fabric and the plastic film off from each other just along the joined zones and properly disconnect the front and rear waist regions from each other. However, this will be rarely achieved and, in many cases, the front and rear waist regions of the pant will be disconnected from each other with the nonwoven fabric and the plastic film torn not along the joined zones but around the joined zones. In other words, the mother intending to take the pant off from the wearer's body must tear apart at least two or three layers of the sheet material at once with a considerable force. In addition to this inconvenience, it may be difficult for a caregiver of the wearer to achieve this operation quickly since it will be rare that these layers of the sheet material are rectilinearly torn apart. Assumed that the waist surrounding elastic members and the leg-surrounding elastic members are attached in a stretched state to the pant, respectively, these elastic members may be peeled off from the nonwoven fabric and the plastic film and thereupon intensely contract just as the side edges of the pants are torn apart. These elastic members peeled off in this manner may painfully hit against the fingertips of the caregiver.

The diaper disposed in REFERENCE 2 is said to ensure that the stretchable "panels" can be removed from the "chassis" along the joint lines of the "panels" and the "chassis". However, on the assumption that these joint lines are formed by heat-sealing the stretchable "panels" with the "chassis", operation of removing the "panels" from the "chassis" will really comprises, just like in the case of the pant disclosed in REFERENCE 1, operation of tearing the "panels" and/or the "chassis" along the joint lines. Such operation will require a considerable force and it may be difficult for the caregiver to achieve this operation quickly. Assumed that the stretchable "panels" include thread-like elastic members attached in a stretched state thereto, these elastic members intensely contract just as these "panels" are removed, and may painfully hit against the fingertips of the caregiver.

In the case of the diaper disclosed in REFERENCE 3, the tear-apart lines used to develop the diaper by tearing the front waist region apart from the rear waist region extend across the elastic members attached to the peripheries of the waist-hole and the leg-holes, respectively, by adhesive. With such arrangement, the elastic members may be severed or peeled off from the peripheries of the waist-hole and the leg-holes so as to be left contract, in any case, with the fingertips of the caregiver holding the diaper in order to develop the diaper. However, it is not easy for the caregiver to sever the elastic members and, even if possible, the elastic members may intensely contract upon being severed and painfully hit against the fingertips of the caregiver. This may occur also when the elastic members are peeled off from the peripheries of the waist-hole and the leg-holes, respectively, so as to be left contract.

The disposable undergarment disclosed in REFERENCE 4 specifies the transverse tensile strength of the nonwoven material used for the tear-apart panel adapted to be torn apart with the bare hands of the caregiver. However, when the pants-type wearing article is taken off from the wearer's body, it is usual to tear apart the transversely opposite lateral portions in the vertical direction and not usual to tear apart these lateral portions by pulling the wearing article. In other words, selection of the material for the tear-apart panels based on the transverse tensile strength is inappropriate to ensure that the wearing article can be easily or smoothly torn apart.

SUMMARY OF THE INVENTION

In view of the problems as have been described above observed when the conventional wearing article is taken off from the wearer's body, it is an object of the present invention to improve the known disposable pull-on wearing article.

According to the present invention, there is provided a disposable pull-on wearing article having a vertical direction, a back-and-forth direction and a transverse direction being orthogonal one to another, the article comprising an annular waist region having a front section and a rear section and extending to form a waist-hole and a crotch region being contiguous to a bottom of the annular waist region and cooperating with the waist-hole to form a pair of leg-holes, and the annular waist region being provided with tear-apart lines extending from the waist-hole to the leg-holes in the vertical direction so that the annular waist region can be torn apart.

The article further comprises a pair of connector sheets used to connect front and rear sections separated from each other being provided in vicinities of transversely opposite lateral portions of the annular waist region, the connector sheets extending in the vertical direction from the waist-hole to respective the leg-holes and being permanently joined at respective joint zones provided on the connector sheets to the front section and the rear section in vicinities of the transversely lateral portions opposed one to another in a circumferential direction of the annular waist region, the connector sheets being respectively provided between respective sets of the joint zones with non-joint zones to be left free from the front section as well as from the rear section, and a tensile strength of the non-joint zones is set to at least 8N/25 mm width in the circumferential direction and a tear strength of the non-joint zones is set in a range of 0.1 to 12N in the vertical direction both lower than those of the transversely opposite lateral portions of the front and rear sections so that the tear-apart lines can be reliably defined.

According to one preferred embodiment of the invention, at least one of the front and rear sections is provided with an elastic member extending along a waist line and a segment of the elastic member extending between the joint zones is attached in a stretched state thereto but remaining segments extending toward the ears beyond the joint zones are attached thereto not in a stretched state.

According to another preferred embodiment of the invention, the crotch region is provided with elastic members attached in a stretched state thereto so as to extend around the leg-holes but not to the connector sheets.

According to still another preferred embodiment of the invention, the connector sheets are formed from a material selected from the group consisting of a nonwoven fabric made of thermoplastic synthetic fibers, a film made of thermoplastic synthetic resin and a laminated sheet comprising the nonwoven fabric and the film.

In the pull-on wearing article according to the present invention, the waist region is provided in the vicinities of the transversely opposite lateral portions with a pair of connector sheets adapted to connect the transversely opposite lateral portions of the front section to the transversely opposite lateral portions of the rear section and to facilitate formation of the tear-apart lines. This unique arrangement allows the used diaper soiled with bodily discharges to be quickly taken off from the wearer's body merely by tearing apart these sheet strips.

According to the embodiment of the invention (1), while the wearing article includes the elastic member extending in the direction of the waist line and attached in a stretched state thereto, this elastic member provided on the front section or the rear section extends not to the connector sheets. Therefore, it is unlikely that the presence of the elastic member extending along the waist line might make it difficult to tear apart these sheet strips in the vertical direction.

Also in the embodiment of the invention (2), the elastic members extending around the leg-holes extend not to the connector sheets. Therefore, there is no anxiety that the presence of the elastic members extending around the leg-holes might make it difficult to tear apart these sheet strips.

According to the embodiment of the invention (3), the stock material for the connector sheets may be selected from the group consisting of a nonwoven fabric made of thermoplastic synthetic resin fibers, a film of thermoplastic synthetic resin, and a laminated sheet comprising these nonwoven fabric and film.

DETAILED DESCRIPTION OF THE PREFERRED EMBODIMENTS

Details of a disposable pull-on wearing article will be more fully understood from the description of a disposable pull-on diaper as a typical embodiment of the invention given hereunder with reference to the accompanying drawings.

Figure 1:
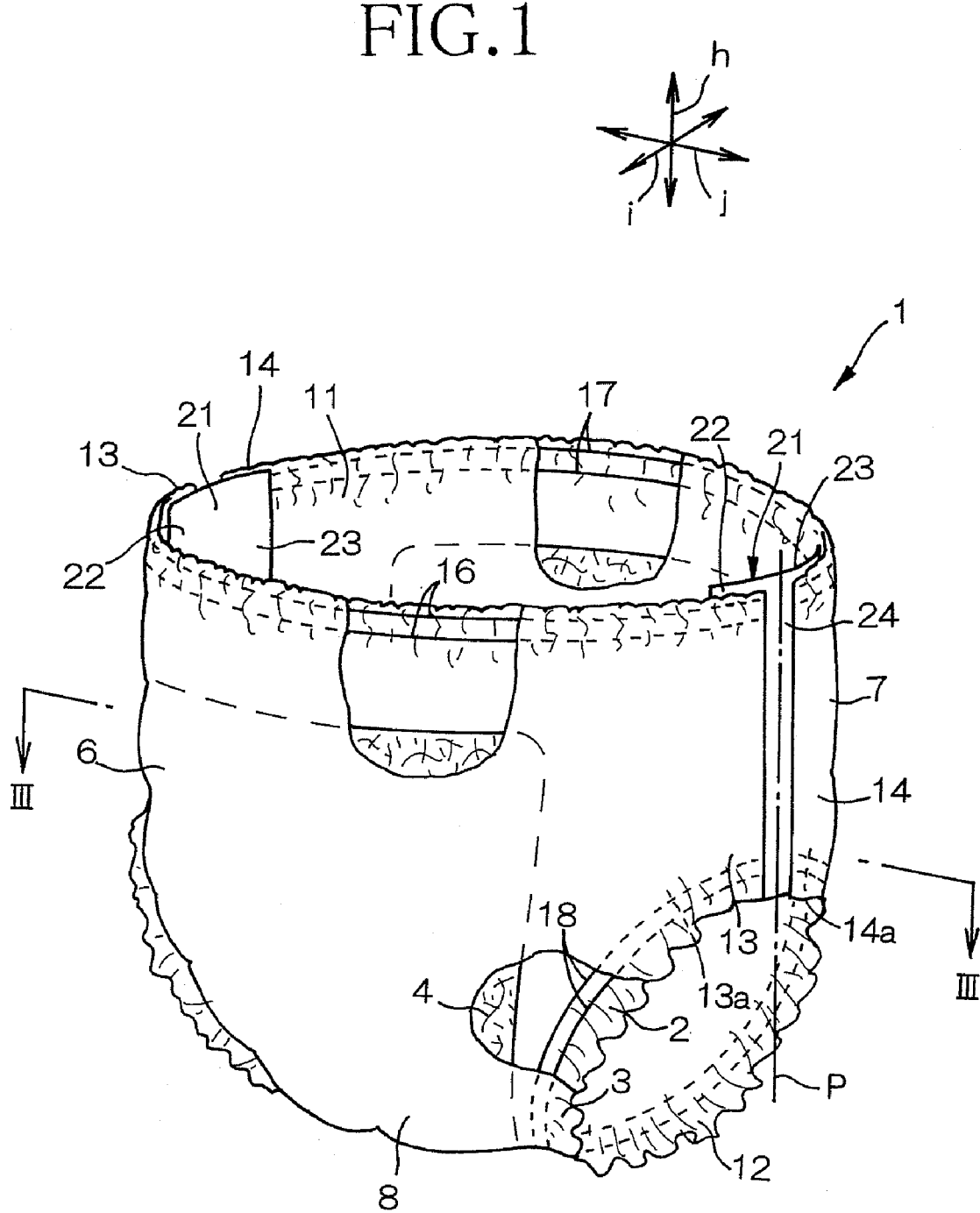
FIG. 1 is a partially cutaway perspective view showing a pull-on diaper.
Figure 2:
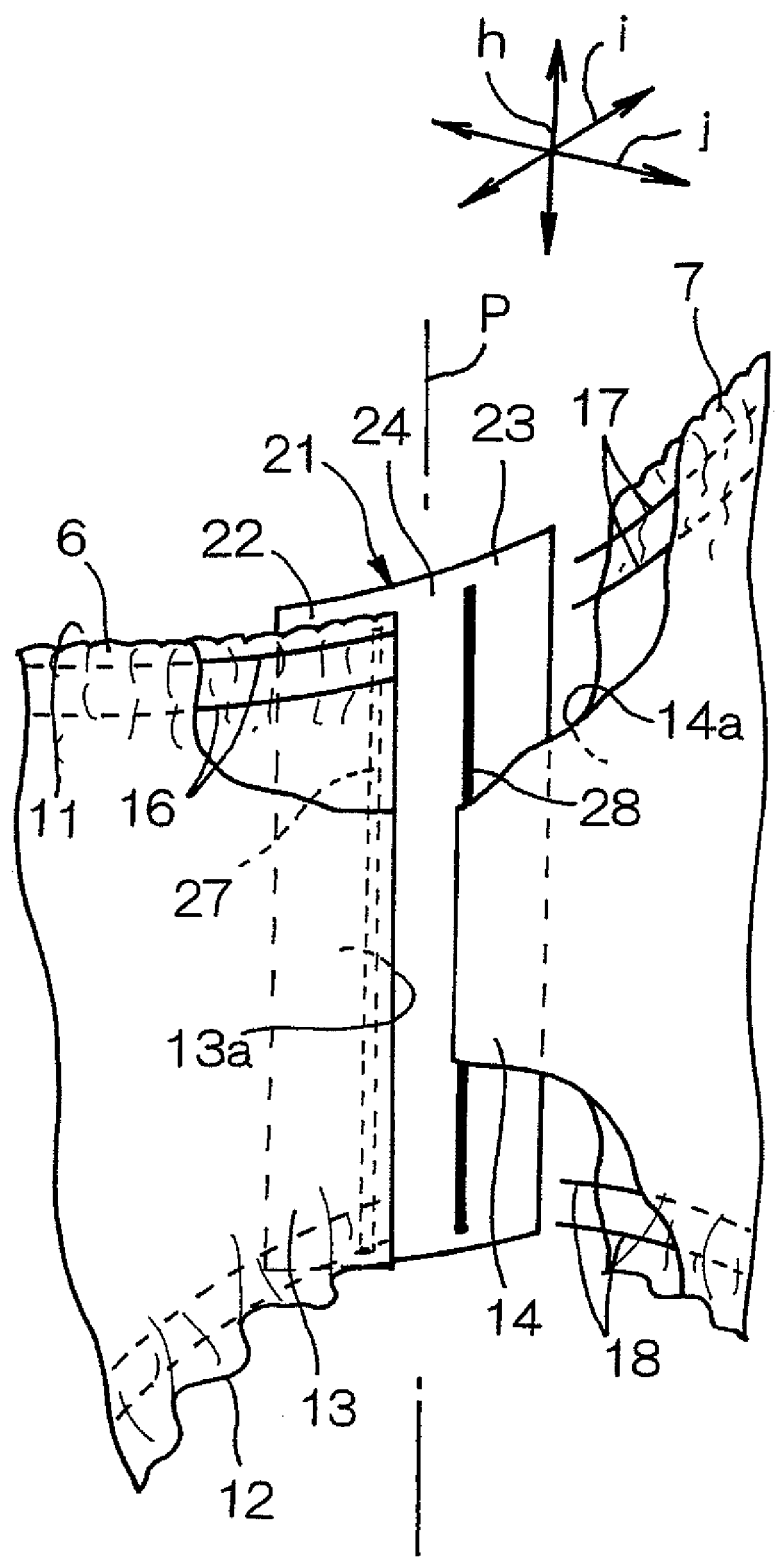
FIG. 2 is an enlarged perspective view partially showing the pull-on diaper.
Figure 3:
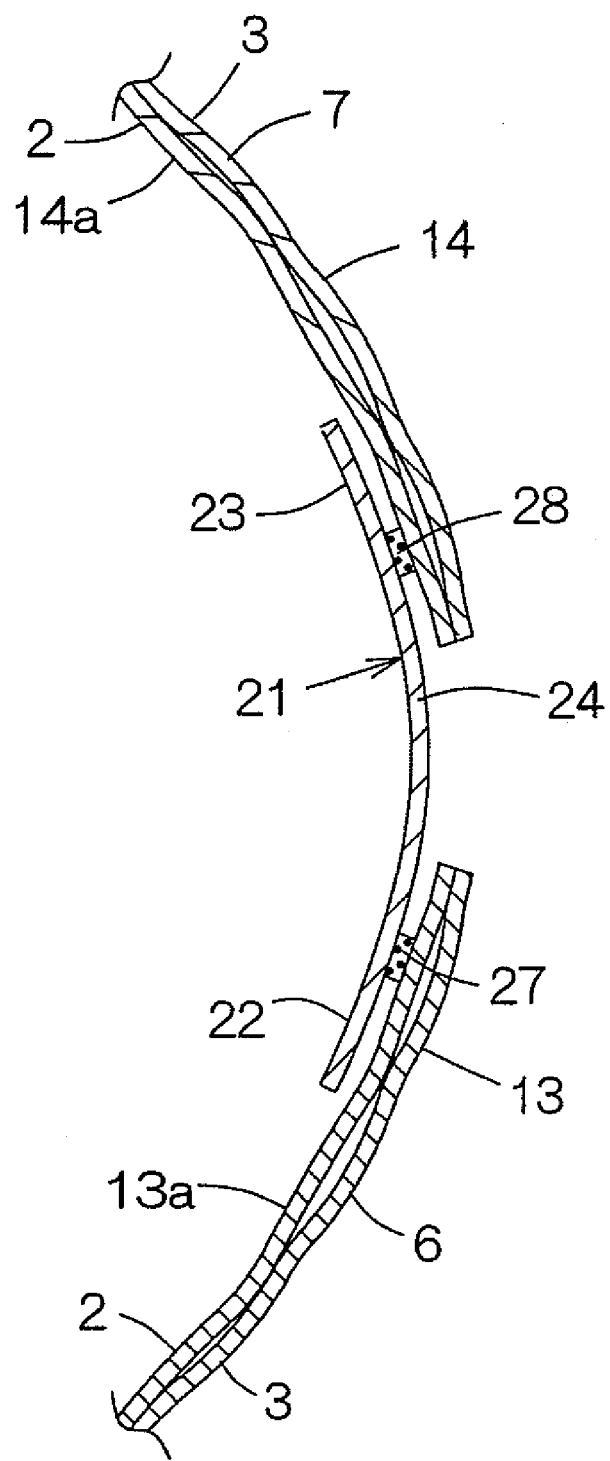
FIG. 3 is a partial sectional view taken along the line III-III in FIG. 1.

FIG. 1 is a perspective view showing a pull-on diaper 1, FIG. 2 is a partial view showing the pull-on diaper 1 and FIG. 3 is a partial sectional view taken along the line II-II in FIG. 1. In FIGS. 1 and 2, the diaper 1 is shown as partially cutaway. The diaper 1 illustrated herein is composed of a liquid-pervious topsheet 2, a liquid-impervious backsheet 3 and a body fluid absorbent core 4 sandwiched between these two sheets 2, 3. The diaper 1 is configured to define a front waist region 6, a rear waist region 7 and a crotch region 8 destined to cover a front waist region, a rear waist region and a crotch region of the wearer. In the respective regions 6, 7, 8, both the topsheet 2 and the backsheet 3 extend outward beyond a peripheral edge of the core 4 and are joined to each other by hot melt adhesives (not shown) in the respective regions thereof extending outward beyond the peripheral edge of the core 4. Along transversely opposite side edges of the diaper 1, each pair of the lateral portions 13, 14 of the front waist region 6 and the rear waist region 7, respectively, are circumferentially adjacent to each other in a direction of the waist line and connected to each other with interposition of a connector sheet 21. Consequentially, the front and rear waist regions 6, 7 are annularly connected to each other whereupon the front and rear waist regions 6, 7 form a waist-hole 11. The front and rear waist regions 6, 7 are provided with elastic members 16, 17 attached in a stretched state thereto along the periphery of the waist-hole 11 so as to extend along substantially full width of the front and rear waist regions 6, 7, respectively. These elastic members 16, 17 are sandwiched between the topsheet 2 and the backsheet 3 and joined to at least one of these sheets 2, 3 by hot melt adhesives (not shown). The front and rear waist regions 6, 7 cooperate with the crotch region 8 to form a pair of leg-holes 12. In the crotch region 8, a leg surrounding elastic member 18 extends along a peripheral edge of this leg-hole 12 between the topsheet 2 and the backsheet 3 and joined in a stretched state to at least one of these sheets 2, 3 by hot melt adhesives (not shown). The diaper 1 has a vertical direction, a back-and-forth direction and a transverse direction designated by h, i and j, respectively, and a waist surrounding direction along which the peripheral edge of the waist-hole 11 extends.

Figure 4:
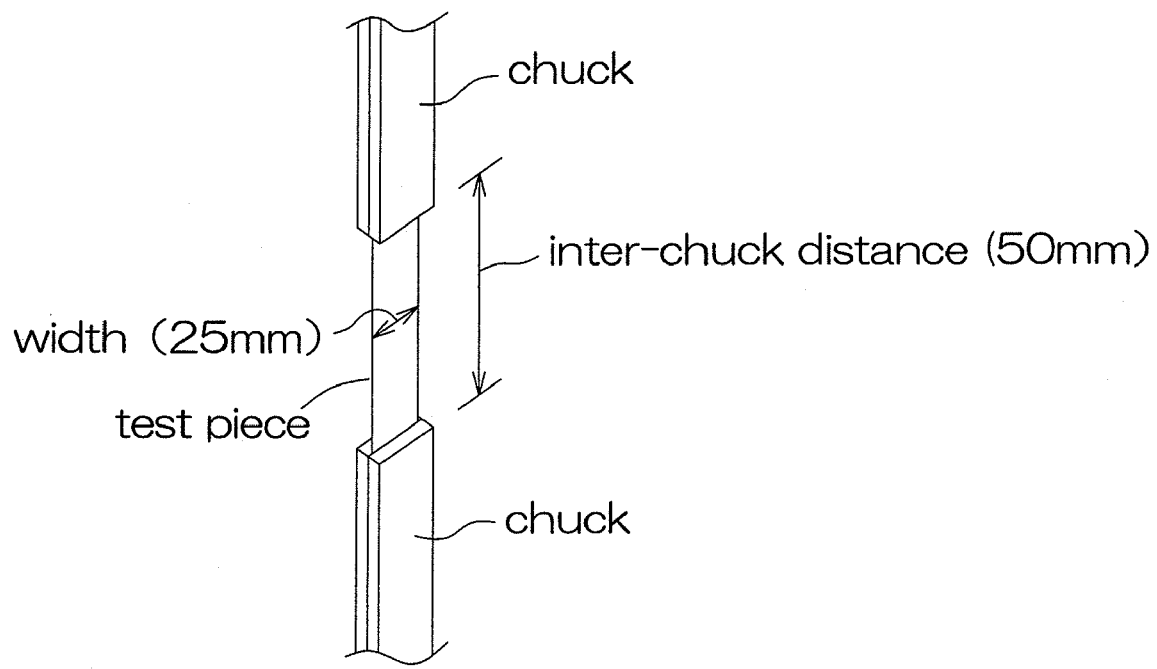
FIG. 4 is a diagram schematically illustrating how to measure a tensile strength.
Figure 5:
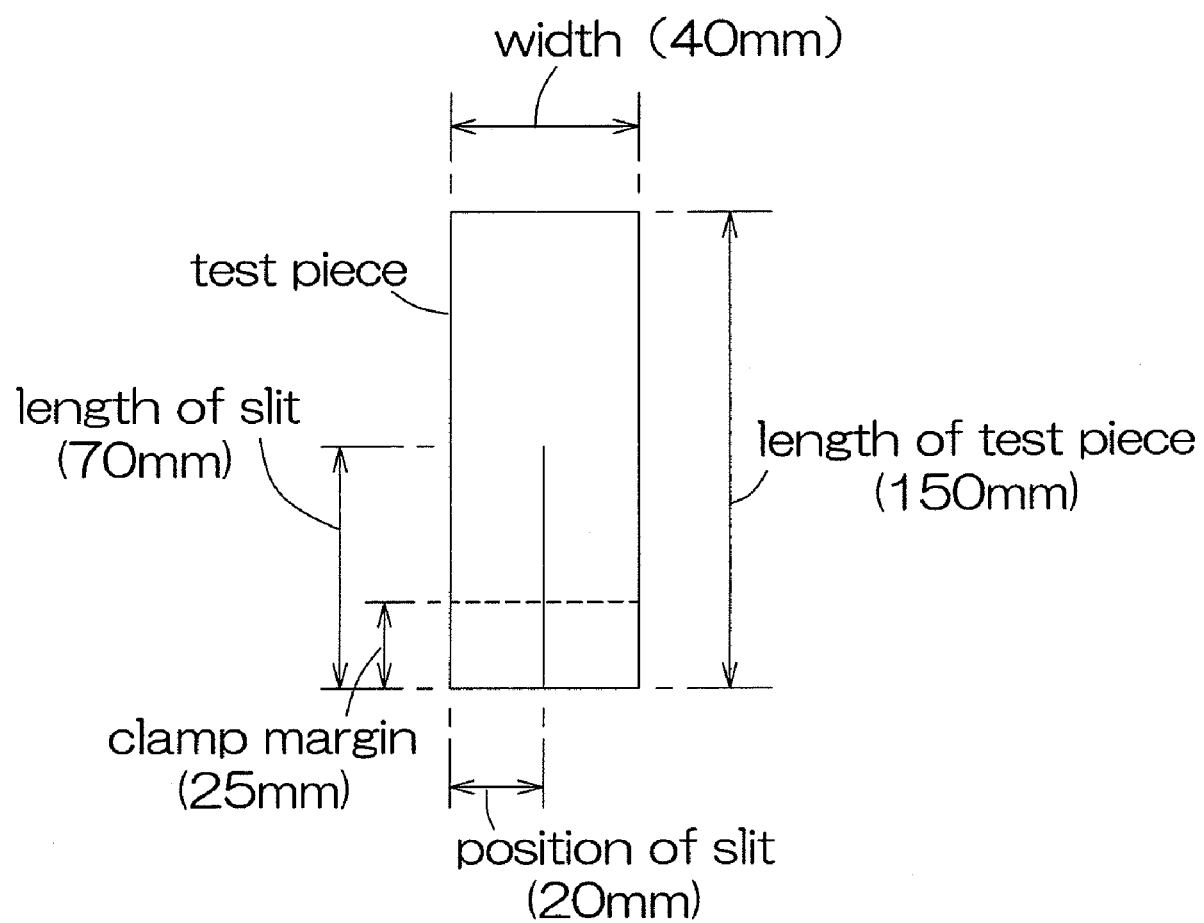
FIG. 5 is a diagram schematically illustrating a test piece used for measurement of a tear strength.
Figure 6:
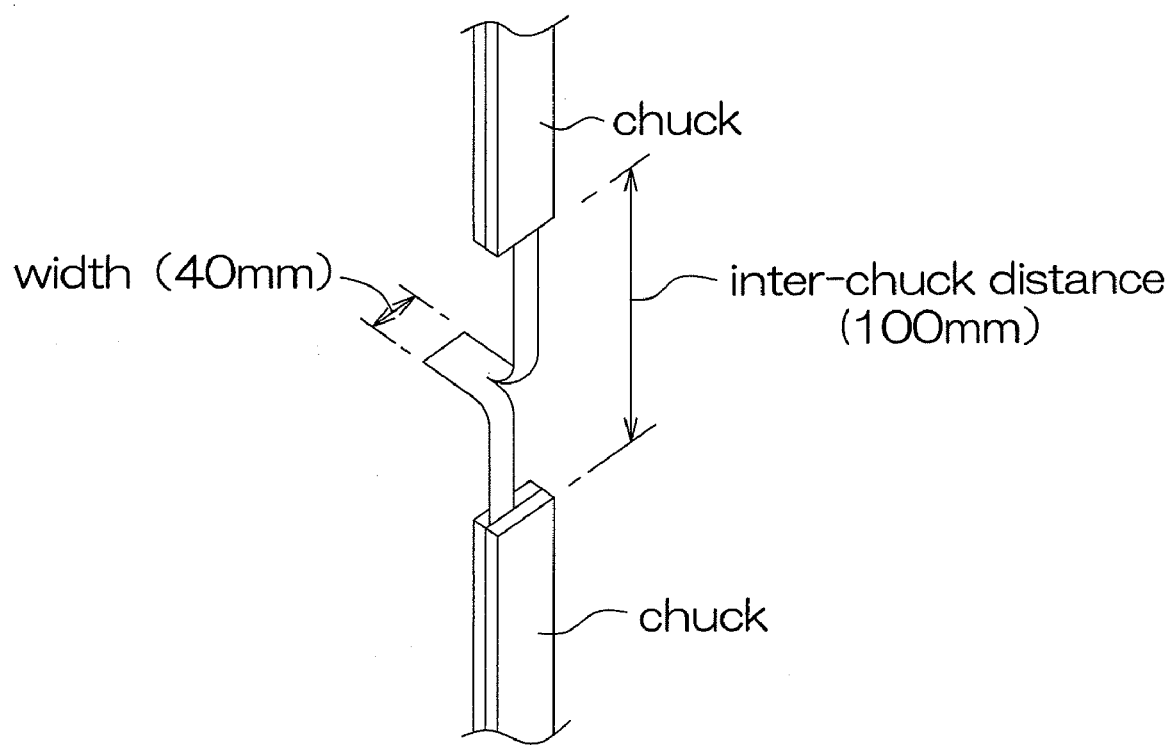
FIG. 6 is a diagram schematically illustrating how to measure a tear strength.

Each of connector sheets 21 adapted to connect the front waist region 6 and the rear waist region 7 cooperating with each other to form the annular waist region is provided in vicinities of its front side edge 22 and rear side edge 23 as viewed in the waist surrounding direction with joint zones 27, 28 (See FIGS. 2 and 3) to be releasably joined to respective inner surfaces 13b, 14b of the lateral portions 13, 14 and further provided between these joint zones 27, 28 with a non-joint zone 24 to be left free from both the front region 6 and the rear regions 7. The non-joint zone 24 extends between the waist-hole 11 and the leg-hole 12 in the vertical direction h. The connector sheet 21 has in the non-joint zone 24 thereof a tensile strength and a tear strength which are measured in manners as illustrated in FIGS. 4 through 6. Specifically, in order to prevent the non-joint zone 24 from being easily broken even if the non-joint zone 24 is strained in the waist surrounding direction as the diaper is put on the wearer's body, the non-joint zone 24 preferably has the tensile strength of at least 8N/width of 25 mm in the waist surrounding direction. The non-joint zone 24 of the connector sheet 21 is adapted to be easily and smoothly torn in the vertical direction h along a straight line from the waist-hole 11 to the leg-hole 12 when the diaper 1 is taken off from the wearer's body. To make this possible, the non-joint zone 24 preferably has the tear strength of 0.1 to 12N in the vertical direction h. As shown, the non-joint zone 24 functioning in this manner includes none of the waist-surrounding members 16, 17 and the leg-surrounding members 18, so it is unlikely that the presence of these elastic members 16, 17, 18 might make it difficult to tear apart the non-joint zone 24 in the vertical direction h. In addition, there is no anxiety that the elastic members might acutely hit against the fingertips of a caregiver to the wearer tearing apart the diaper 1 upon intense contraction of the elastic members having been in a stretched state contract as the conventional pull-on diaper has been the case. The diaper 1 may be alternatively implemented, wherein the connector sheets 21 present a color distinguished from that of the ears 13a, 14a so that the non-joint zones 24 of the respective connector sheets 21 can be easily identified.

A stock material for the topsheet 2 may be selected from the group consisting of a nonwoven fabric made of thermoplastic synthetic resin fibers with a basis weight of 10 to 30 g/m$^2$ and a monoaxially or biaxially oriented porous film made of thermoplastic synthetic resin with a thickness of 10 to 30 μm.

As stock material for the backsheet 3 may be selected from the group, for example, consisting of a biaxially oriented film made of thermoplastic synthetic resin with a thickness of 20 to 50 μm and a composite sheet comprising such film and nonwoven fabric made of thermoplastic synthetic resin fibers with a basis weight of 20 to 50 g/m$^2$ which are intermittently joined to each other.

The body fluid absorbent core 4 may be formed from a mixture of fluff pulp and super-absorbent polymer particles wrapped with a sheet material such as a tissue paper or a nonwoven fabric having high liquid-permeability and high liquid-diffusivity, or fluff pulp wrapped with such sheet material.

Along the transversely opposite lateral portions 13, 14 of the front and rear waist regions 6, 7, respectively, the topsheet 2 and the backsheet 3 are joined together by adhesion or heat-sealing technique to form the composite sheet and/or this composite sheet includes the elastic members 16, 17 extending along the front and rear waist lines as well as the leg-surrounding elastic members 18. Therefore, the transversely opposite lateral portions 13, 14 have the tensile strength and the tear strength both higher than those of the connector sheets 21 and it is unlikely that these lateral portions 13, 14 might be torn easier than the connector sheets 21 when the diaper 1 is taken off from the wearer's body. In the case of the diaper 1 according to the invention, the lateral portions 13 and/or the lateral portions 14 may be formed from one of the topsheet 2 and the backsheet 3 so far as one of these topsheet and backsheet 3 has the tensile strength as well as the tear strength higher than those of the connector sheet 21. Furthermore, the lateral portions 13 and/or the lateral portions 14 may be formed from a third sheet provided separately of both the topsheet 2 and the backsheet 3 and having the tensile strength as well as the tear strength higher than the connector sheet strip 21. The lateral portions 13, 14 are joined together by heat-sealing technique or adhesion along the respective joint zones 27, 28 with a sufficiently high peel strength to eliminate the possibility that the lateral portions 13, 14 might be peeled off from each other as the diaper 1 is put on or taken off from the wearer's body.

FIG. 4 is a diagram illustrating a method for measurement of tensile strength presented by the sheet material used as the connector sheet strip 21 together with a test piece used for this measurement. The test piece is made so as to have its longitudinal direction in conformity with the waist line of the diaper 1 and attached to the tensile tester with an inter-chuck distance of 50 mm. This test piece is stretched at a stress rate of 200 mm/min to determine a value of the ultimate load until a moment of breakage as the tensile strength.

FIGS. 5 and 6 are diagrams illustrating a method for measurement of a tear strength presented by the sheet material used as the connector sheet 21 together with a test piece used for this measurement, respectively. The test piece is made so as to have longitudinal directions of the test piece and its slit in conformity with the vertical direction h of the diaper 1 and attached to the tensile tester with an inter-chuck distance of 100 mm along clamp margins each of approximately 25 mm. This test piece is stretched at a stress rate of 200 mm/min to determine a value of the ultimate load until a moment of breakage as the tear strength. Preferred sheet material used for the connector sheets 21 has a tear strength in a range of 0.1 to 12N.

Figure 7:
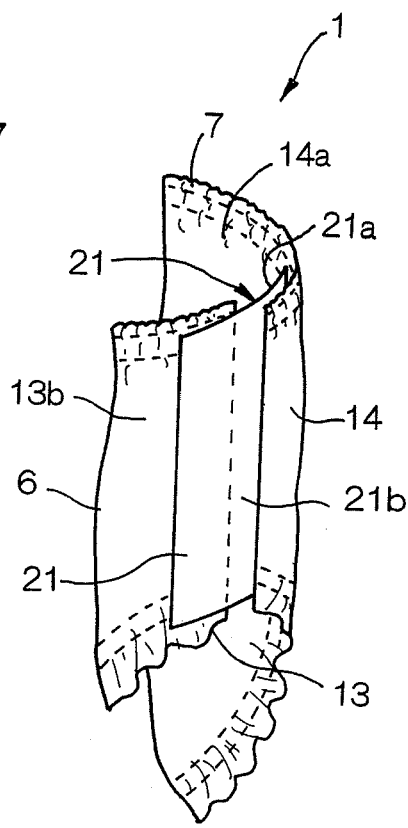
FIG. 7 is a view similar to FIG. 2, showing one preferred embodiment of the invention.
Figure 8:
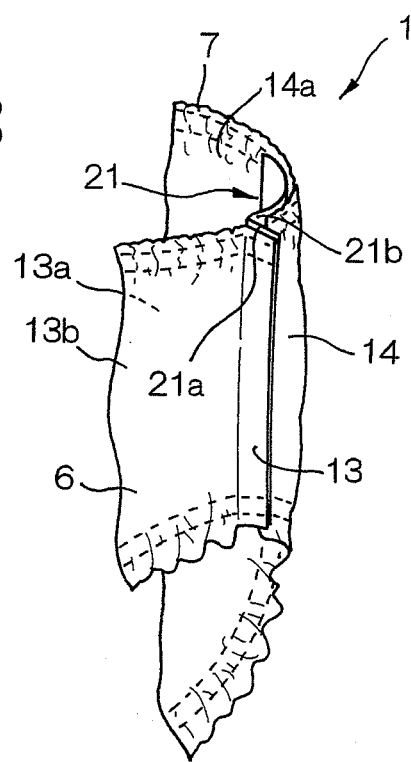
FIG. 8 is a view similar to FIG. 2, showing another preferred embodiment of the invention.
Figure 9:
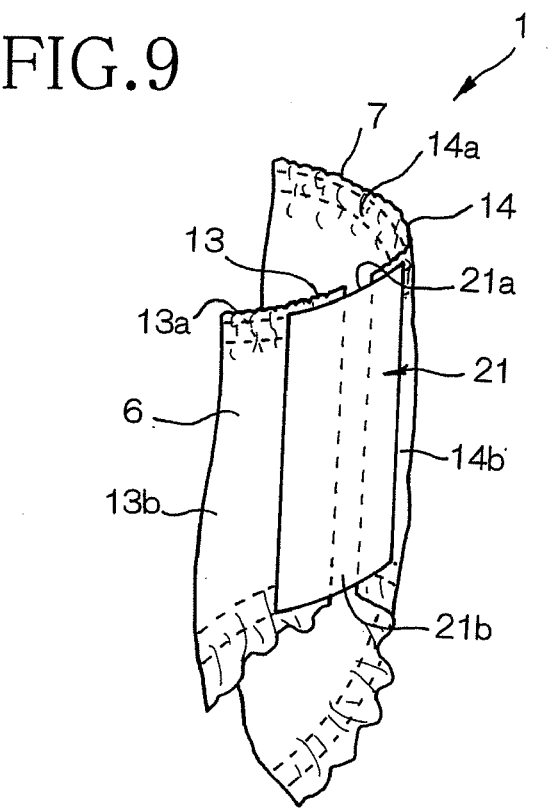
FIG. 9 is a view similar to FIG. 2, showing still another preferred embodiment of the invention.

FIGS. 7, 8 and 9 are views similar to FIG. 2, partially showing other embodiments of the present invention. In the case of this diaper 1, the connector sheets 21 have respective inner surfaces 21a joined to the outer surface 13b of the front waist region 6 along the transversely opposite lateral portions thereof and respective outer surfaces 21b joined to the inner surface 14a of the rear waist region 7 along the transversely opposite lateral portions thereof. In the case of the diaper 1 shown by FIG. 8, the connector sheets 21 have respective inner surfaces 21a joined to the inner surface 13a of the front waist region 6 along the transversely opposite lateral portions thereof and respective outer surfaces 21b joined to the inner surface 14a of the rear waist region 7 along the transversely opposite lateral portions thereof. In the case of the diaper 1 shown in FIG. 9, the connector sheets 21 have respective inner surfaces 21a joined to the respective outer surfaces 13b, 14b of the front and rear waist regions 6, 7 along the transversely opposite lateral portions thereof. The manner in which the connector sheets 21 are joined to the front and rear waist regions 6, 7 along the transversely opposite lateral portions of these both regions 6, 7 may be selected depending on the system for making the diaper 1.

Figure 10:
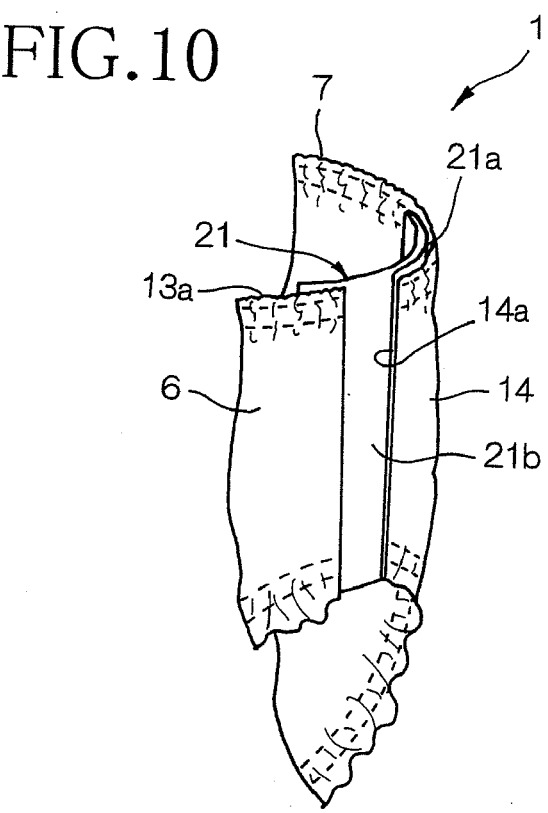
FIG. 10 is a view similar to FIG. 2, showing yet another preferred embodiment of the invention.

FIG. 10 also is a view similar to FIG. 2, partially showing an alternative embodiment of the present invention. In the case of this diaper 1, the connector sheets 21 joined to the inner surface 13a of the front waist region 6 along the transversely opposite lateral portions and extending into the rear waist region 7 are folded back in the rear waist region 7 and the connector sheets 21 folded back in this manner have respective inner surfaces 21a joined to the inner surface of the rear waist region 7 along the transversely opposite lateral portions thereof.

Figure 11:
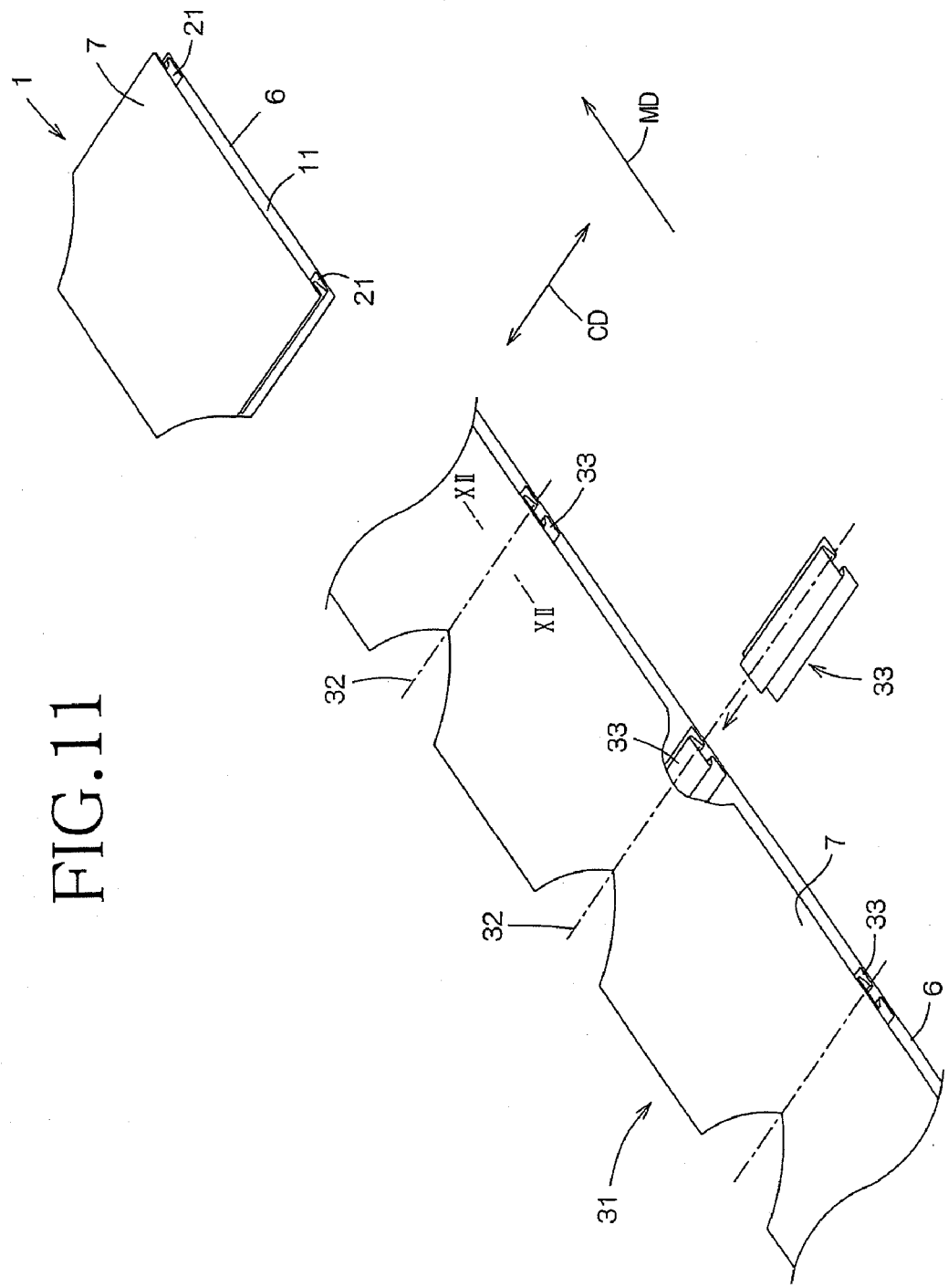
FIG. 11 is a diagram partially illustrating a process for making the pants-type diaper.
Figure 12:
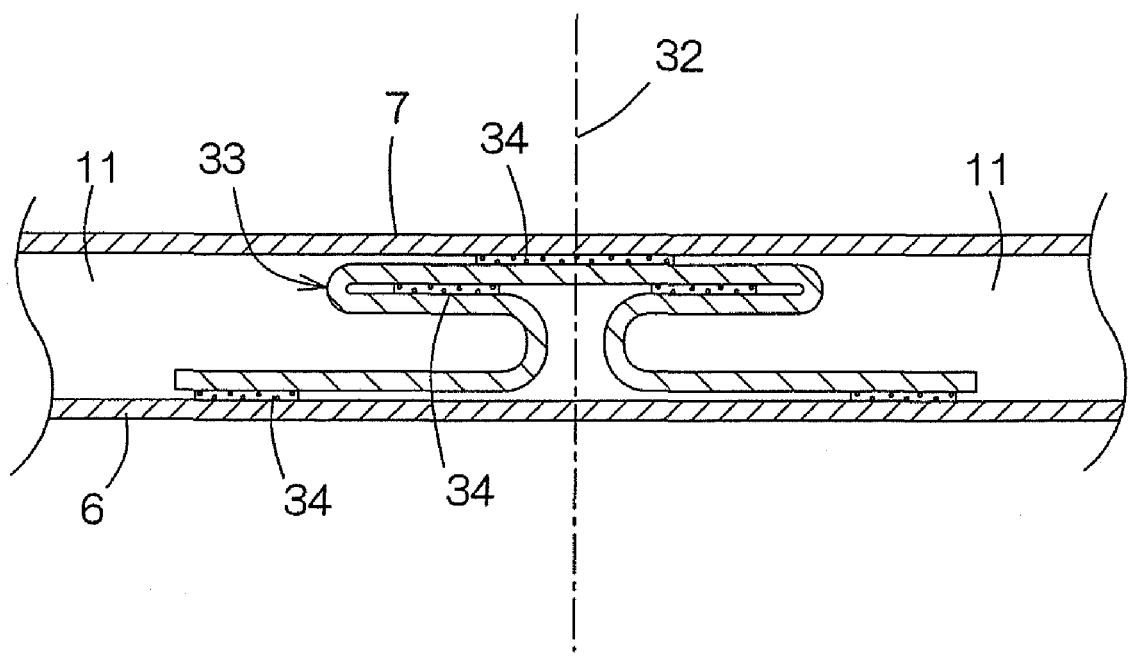
FIG. 12 is a sectional view taken along the line XII-XII in FIG. 11.

FIG. 11 is a diagram partially illustrating a process for continuously manufacturing the diaper of FIG. 10 and FIG. 12 is a sectional view taken along the line XII-XII in FIG. 11. In the process partially illustrated in FIG. 11, continuous band 31 comprising diapers 1 not cut off one from another wherein each diaper 1 has been folded so as to place the front and rear waist regions 6, 7 upon each other runs in a machine direction MD, i.e., from the left toward the right as viewed in FIG. 11. The continuous band 31 is successively cut along guide lines 32 extending in a cross direction CD which is orthogonal to the machine direction MD and thereby the individual diapers 1 are obtained. Between the front waist regions 6 and the rear waist regions 7 of the individual diapers 1 in the continuous band 31, base materials 33 destined to become the connector sheets 21 for the individual diapers 1 extend along the respective guide lines 32. As will be apparent from FIG. 12, each of the base materials 33 has a substantially Ω-shaped cross-section and is joined to the front and rear waist regions 6, 7 by hot melt adhesive 34. It will be also apparent from FIG. 12 that each of the base materials 33 is joined between its part and part by hot melt adhesive 34 to maintain its Ω-shaped cross-section. The front and rear waist regions 6, 7 are deformed so as to open the waist-hole 11 largely as seen in FIG. 1 as the base materials 33 are cut along the guide lines 32. Consequentially, the connector sheet 21 is obtained, which presents a unique shape as seen in FIG. 10.

Figure 13:
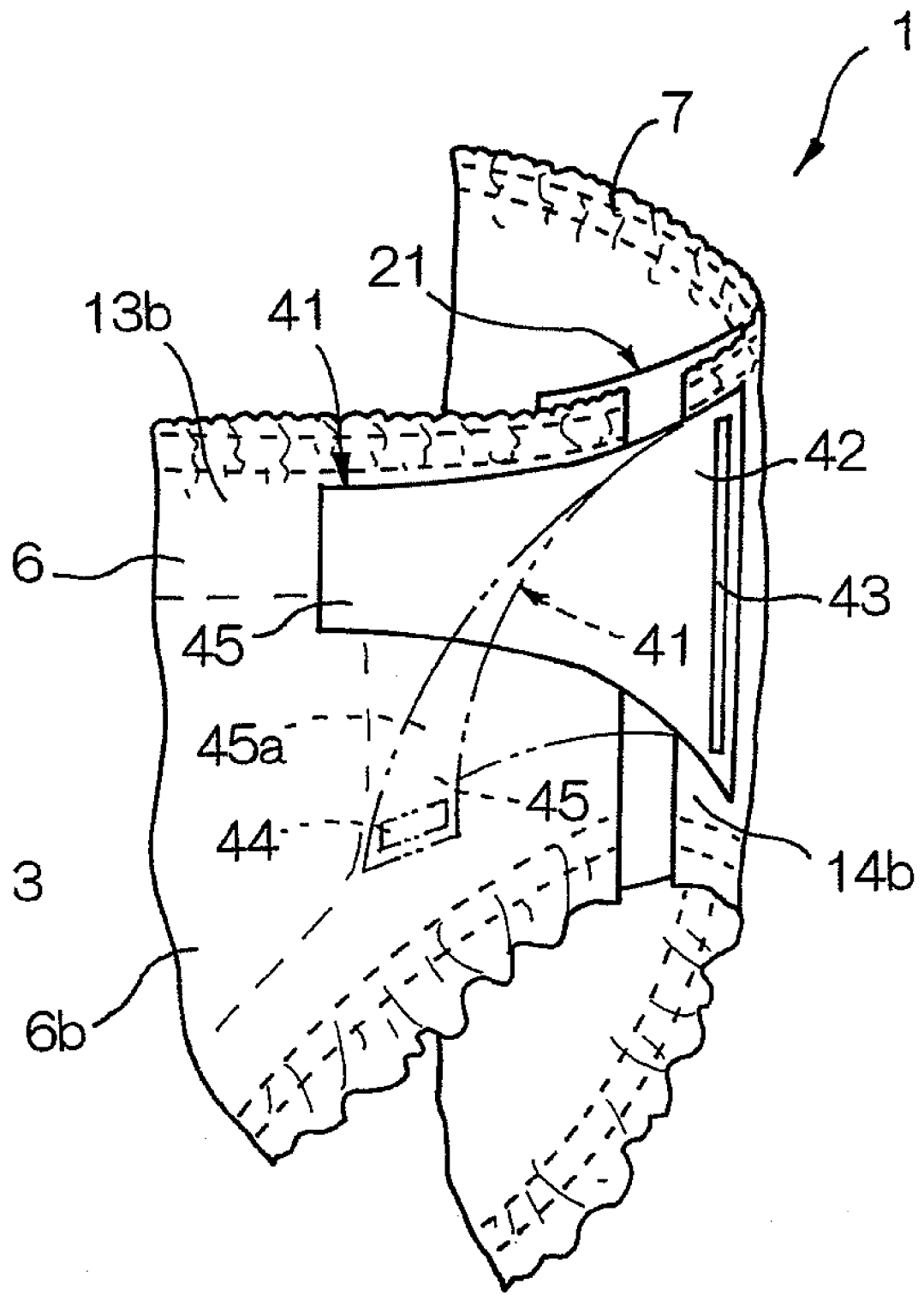
FIG. 13 is a view similar to FIG. 2, showing further another preferred embodiment of the invention.

FIG. 13 also is a view similar to FIG. 2, showing an embodiment of the present invention. This diaper 1 includes, in addition to the connector sheets 21 used to connect the front and rear waist regions 6, 7 with each other, a pair of tape fasteners 41 each having a rear end 42 permanently joined to the outer surface 14b of the rear waist region 7 along the joint zone 43 and a front end 45, which is opposite to the rear end 42 as viewed in the waist-surrounding direction, releasably, i.e., temporarily joined directly to the outer surface of the backsheet 3 or to a target zone (not shown) formed on the outer surface of the backsheet 3 in the front waist region 6. The front end 45 of the tape fastener 41 is adapted to be peeled off from the front waist region 6 as indicated by imaginary lines and this front end 45 is, as shown, provided on its inner surface 45a with a landing zone 44 formed from pressure-sensitive adhesive or a hook member constituting a so-called mechanical fastener. Such tape fastener 41 can be advantageously used in order to put the diaper 1 around the wearer's waist with desired fit, to put the diaper 1 again on the wearer's body after the connector sheets 21 have been torn apart and to roll up the diaper 1 having been taken off from the wearer's body for disposal.

While the present invention has been described hereinabove with respect to the disposable pull-on diaper, this invention may be applicable to the other disposable wearing article such as training pant(s), pant(s) for incontinent patient or sanitary shorts. In any one of the illustrated embodiments, the connector sheets 21 are provided in the vicinities of the transversely opposite lateral portions of the diaper 1 in the manner such that each of the connector sheets 21 is substantially bisected and the front half is provided on the front waist region 6 and the rear half is provided on the rear waist region 7. However, positions at which the connector sheets 21 are provided are not specified. Specifically, it is also possible without departing from the spirit and the scope of the invention to provide the connector sheets 21 optionally at the positions put aside from the lateral portions of the waist region toward the wearer' abdomen or back as far as the connector sheets 21 divide the waist region into the front section and the rear section.

EXAMPLE

From the commercially available pull-on disposable diaper (Moony Man (Trademark) M-size manufactured by the present applicant), wherein the front and rear waist regions are put flat and welded together along transversely opposite side lateral portions thereof, these lateral portions each approximately 15 mm in the transverse direction of the diaper were cut off to disconnect the front and rear waist regions, then connector sheets made of various types of sheet materials were welded to the front and rear waist regions so as to connect these front and rear waist regions again and thereby diapers substantially configured as seen in FIG. 1 were obtained. Each of these diapers obtained in this manner was put on the lay figure adapted to M-size by stretching the diaper in the waist's circumferential direction so as to enlarge the waist-hole. It was observed whether the connector sheet was more or less torn apart during operation of putting the diaper on the layer figure. At the same time, with respect to the various used sheet materials used for this test, tensile strength in the transverse direction was measured and the tensile strength of the sheet material which was not torn apart during putting the diaper on the layer figure was determined at the strength as the connector sheet. Evaluation result for various types of sheet material and the diapers using them is listed by TABLE 1. Degree of resistance felt by the hands when the connector sheets were torn apart downward in the vertical direction with the hands to take the diaper off from the wearer's body were sensuously determined. For this determination, on the basis of the evaluation score 3 representing a degree of resistance exhibited by the commercially available diaper when the welded lateral portions of the front and rear waist regions were torn apart, degrees of resistance exhibited by the connector sheets made of various sheet materials when these connector sheets were torn apart were evaluated in the manner as follows:

Evaluation score 1: tear-resistance remarkably higher than in the case of the commercially available diaper.
Evaluation score 2: tear-resistance slightly higher than in the case of the commercially available diaper.
Evaluation score 3: tear-resistance exhibited by the the control.
Evaluation score 4: tear-resistance slightly lower than in the case of commercially available diaper.
Evaluation score 5: tear-resistance significantly lower than in the commercially available diaper.
Evaluation score 6: tear-resistance appreciably lower than in the commercially available diaper.
Evaluation score 7: tear-resistance remarkably lower than in the case of the commercially available diaper.

TABLE 1

| Sheet material used for connector sheets | Description | Basis weight (g/m$^2$) | Thickness (μm) | Fineness (dtex) | Evaluation of sheet material Tensile strength (N) AVE | Tear strength (N) AVE | Evaluation of diaper Break of connector sheets when put on | Tear resistance of connector sheet when taken off |
|---|---|---|---|---|---|---|---|---|
| Material | | | | | | | | |
| Film (1) | Monoaxially oriented breathable · moisture-permeable PE film | 22 | 20 | — | 2.78 | 0.19 | Observed | 7 |
| Film (2) | Biaxially oriented breathable · moisture-permeable PE film | 22 | 20 | — | 5.08 | 0.33 | Observed | 6 |
| Film (3) | Biaxially oriented air-impermeable PE film | 21 | 32 | — | 4.07 | 0.30 | Observed | 6 |
| Film (4) | Biaxially oriented air-impermeable PE film | 23.5 | 32 | — | 8.36 | 3.21 | Not observed | 5 |
| Nonwoven fabric (1) | SB nonwoven fabric of PP | 18 | 180 | 2.0 | 8.15 | 7.42 | Not observed | 5 |
| Nonwoven fabric (2) | SB nonwoven fabric of PP | 40 | 460 | 2.5 | 35.81 | 17.96 | Not observed | 3 |
| Nonwoven fabric (3) | SMS nonwoven fabric of PP (SB layer 4.5 g/m$^2$:melt-blown layer 1 g/m$^2$:SB layer 4.5 g/m$^2$) | 10 | 90 | 2.0 | 4.80 | 5.00 | Observed | 6 |
| Nonwoven fabric (4) | SMS nonwoven fabric of PP (SB layer 11.5 g/m$^2$:melt-blown layer 2 g/m$^2$:SB layer 11.5 g/m$^2$) | 25 | 250 | 2.2 | 14.02 | 9.71 | Not observed | 4 |
| Laminate sheet (1) | SB nonwoven fabric of PP/Rubber-based hot melt adhesive/biaxially oriented breathable · moisture-permeable PE film | (SB)15/(film)25 | 120 | 2.0 | 9.73 | 5.28 | Not observed | 5 |
| Laminate sheet (2) | SMS nonwoven fabric of PP (SB layer 4.5 g/m$^2$:melt-blown layer 1 g/m$^2$:SB layer 4.5 g/m$^2$) Rubber-based hot melt adhesive/biaxially oriented air-impermeable PE film | (SMS)10/(Film)23.5 | 270 | 2.0 | 12.16 | 8.64 | Not observed | 5 |
| Laminate sheet (3) | SMS nonwoven fabric of PP (SB layer 9 g/m$^2$:melt-blown layer 2 g/m$^2$:SB layer 9 g/m$^2$)Rubber-based hot melt adhesive/biaxially oriented air-permeable PE film | (SMS)20/(Film)23.5 | 380 | 2.0 | 16.98 | 11.98 | Not observed | 4 |

Note (1)
PP: Polypropylene
PE: Polyethylene
SB: spun-bonded
SMS: spun-bonded/melt-blown/spun-bonded
Note (2)
Film (1) was used so that its oriented direction be in conformity with the vertical direction of the diaper.

Of various types of sheet material evaluated, those having obtained the evaluation scores of 4 or higher were determined as appropriate as a stock material for the connector sheet adapted to be more quickly torn apart than in the commercially available diaper as one embodiment of the conventional diaper. The tear strength in the vertical direction of the diaper was measured in connection with these various types of sheet materials and the sheet materials providing acceptable value of the tear strength as described above was determined as the stock material used for the connector sheet. Determined result and evaluation points were listed in TABLE 1. Preferred tensile strength of the sheet material allowing the diaper to be put on the wearer's body without being torn apart and to be easily torn apart when taken off from the wearer's body was at least 8N and preferred tear strength was in a range of 0.1 to 12N.

The present invention makes it possible to produce the pull-on disposable wearing article adapted to be taken off from the wearer's body by easily tearing apart the transversely opposite lateral portions of the waist region.

The entire discloses of Japanese Patent Application No. 2005-173997 filed on Jun. 14, 2005 including specification, drawings and abstract are herein incorporated by reference in its entirety.

What is claimed is:

1. A disposable pull-on wearing article, comprising:
an annular waist region having a front section and a rear section connected together to form a waist-hole;
a crotch region being contiguous to a bottom of said annular waist region and cooperating with said annular waist region to form a pair of leg-holes;
said annular waist region being provided with tearable lines longitudinally extending from said waist-hole to said leg-holes so that the front and rear sections of said annular waist region can be torn apart; and
a pair of connector sheets connecting transversely opposite lateral portions of said front and rear sections, said connector sheets extending in a longitudinal direction of said tearable lines from said waist-hole to respective said leg-holes and each comprising
joint zones permanently joined to the respective transversely lateral portions of said front and rear sections, and
between said joint zones, a non-joint zone free of direct attachment to said front and rear sections and defining one of said tearable lines;
wherein
a tensile strength of said non-joint zones is at least 8N/25 mm width in a circumferential direction of the waist-hole, and
a tear strength of said non-joint zones is in a range of 0.1 to 12N in said longitudinal direction of the tearable lines, and is lower than those of said transversely opposite lateral portions of said front and rear sections so that said tearable lines are reliably defined by the non-joint zones, and
a sheet material of said connector sheets is one selected from the group consisting of:
monoaxially oriented breathable, moisture-permeable polyethylene (PE) film with its orientation arranged along the longitudinal direction of the tearable lines;
biaxially oriented breathable, moisture-permeable PE film;
biaxially oriented air-impermeable PE film;
spun-bonded (SB) nonwoven fabric of polypropylene (PP);
spun-bonded/melt-blown/spun-bonded (SMS) PP nonwoven fabric having a melt-blown (MB) non-woven fabric layer sandwiched between two SB non-woven fabric layers;
laminate of rubber-based hot melt adhesive sandwiched between (i) SB nonwoven fabric of PP and (ii) biaxially oriented breathable, moisture-permeable PE film; and
laminate of rubber-based hot melt adhesive sandwiched between (i) SMS PP nonwoven fabric and (ii) biaxially oriented air-impermeable PE film;
wherein
each of said front and rear sections has opposite inner and outer surfaces wherein the inner surface is directly contactable with a wearer, in use; and
each said connector sheet has opposite inner and outer surfaces, the inner surface having a portion directly contactable with the wearer, in use;
wherein the inner surface of each said connector sheet is directly attached to the outer surface of one of said front and rear sections, and the outer surface of each said connector sheet is directly attached to the inner surface of the other of said front and rear sections.

2. The wearing article as defined by claim 1, wherein at least one of said front and rear sections is provided with an elastic member attached in a stretched state thereto so as to extend substantially fully along the waist-hole but not into said connector sheets.

3. The wearing article as defined by claim 1, wherein said crotch region is provided with elastic members attached in a stretched state thereto so as to extend around said leg-holes but not into said connector sheets.

4. The wearing article as defined by claim 1, wherein the sheet material of said connector sheets is a biaxially oriented air-impermeable PE film.

5. The wearing article as defined by claim 1, wherein the sheet material of said connector sheets is SB nonwoven fabric of PP.

6. The wearing article as defined by claim 1, wherein the sheet material of said connector sheets is SMS PP nonwoven fabric having an MB non-woven fabric layer sandwiched between two SB non-woven fabric layers.

7. The wearing article as defined by claim 6, wherein said MB non-woven fabric layer has a basic weight of 1 $g/m^2$, and each of said SB non-woven fabric layer has a basic weight of 4.5 $g/m^2$.

8. The wearing article as defined by claim 6, wherein said MB non-woven fabric layer has a basic weight of 2 $g/m^2$, and each of said SB non-woven fabric layer has a basic weight of 11.5 $g/m^2$.

9. The wearing article as defined by claim 1, wherein the sheet material of said connector sheets is a laminate of rubber-based hot melt adhesive sandwiched between (i) SB nonwoven fabric of PP and (ii) biaxially oriented breathable, moisture-permeable PE film.

10. The wearing article as defined by claim 1, wherein the sheet material of said connector sheets is a laminate of rubber-based hot melt adhesive sandwiched between (i) SMS PP nonwoven fabric and (ii) biaxially oriented air-impermeable PE film.

11. The wearing article as defined by claim 10, wherein said SMS PP nonwoven fabric includes an MB non-woven fabric layer having a basic weight of 1 $g/m^2$ and being sandwiched between two SB non-woven fabric layers each having a basic weight of 4.5 $g/m^2$.

12. The wearing article as defined by claim 10, wherein said SMS PP nonwoven fabric includes an MB non-woven fabric layer having a basic weight of 2 $g/m^2$ and being sandwiched between two SB non-woven fabric layers each having a basic weight of 9 $g/m^2$.

13. A disposable pull-on wearing article, comprising:
a pair of connector sheets;
a front section and a rear section having respective transversely opposite lateral portions connected together by said connector sheets to form a waist-hole, each of said front and rear sections having opposite inner and outer surfaces wherein the inner surface is directly contactable with a wearer, in use;

a crotch section connecting the front and rear sections and cooperating with said front and rear sections to form a pair of leg-holes;

said connector sheets defining tearable lines extending longitudinally from said waist-hole to said leg-holes so that the front and rear sections can be torn apart;

each of said connector sheets comprising joint zones permanently, directly joined to the respective transversely lateral portions of said front and rear sections, and between said joint zones, a non-joint zone free of direct attachment to said front and rear sections and defining one of said tearable lines;

wherein a tensile strength of said non-joint zones is at least 8N/25 mm width in a circumferential direction of the waist-hole, and a tear strength of said non-joint zones is in a range of 0.1 to 12N in a longitudinal direction of the tearable lines, and is lower than those of said transversely opposite lateral portions of said front and rear sections so that said tearable lines are reliably defined by the non-joint zones;

each said connector sheet has opposite inner and outer surfaces, the inner surface having a portion directly contactable with the wearer, in use;

each said connector sheet is folded along a folding line, that extends in the longitudinal direction of the tearable lines from the waist-hole to the associated leg-hole, into an outer section and an inner section overlapping the outer section;

the outer surface of said connector sheet in the inner section is directly attached to the inner surface of the respective one of the transversely opposite lateral portions of one of said front and rear sections; and the inner surface of said connector sheet in the outer section is directly attached to the inner surface of the respective one of the transversely opposite lateral portions of the other of said front and rear sections.

14. A disposable pull-on wearing article, comprising:

a pair of connector sheets;

a front section and a rear section having respective transversely opposite lateral portions connected together by said connector sheets to form a waist-hole, each of said front and rear sections having opposite inner and outer surfaces wherein the inner surface is directly contactable with a wearer, in use;

a crotch section connecting the front and rear sections and cooperating with said front and rear sections to form a pair of leg-holes;

said connector sheets defining tearable lines extending longitudinally from said waist-hole to said leg-holes so that the front and rear sections can be torn apart;

each of said connector sheets comprising joint zones permanently, directly joined to the respective transversely lateral portions of said front and rear sections, and between said joint zones, a non-joint zone free of direct attachment to said front and rear sections and defining one of said tearable lines;

wherein a tensile strength of said non-joint zones is at least 8N/25 mm width in a circumferential direction of the waist-hole, and a tear strength of said non-joint zones is in a range of 0.1 to 12N in a longitudinal direction of the tearable lines, and is lower than those of said transversely opposite lateral portions of said front and rear sections so that said tearable lines are reliably defined by the non-joint zones;

each said connector sheet has opposite inner and outer surfaces, the inner surface having a portion directly contactable with the wearer, in use, wherein each said connector sheet has the inner surface directly attached to the outer surface of the respective one of the transversely opposite lateral portions of one of said front and rear sections, and the outer surface directly attached to the inner surface of the respective one of the transversely opposite lateral portions of the other of said front and rear sections;

wherein an entire portion of the inner surface of said connector sheet between (i) a longitudinal edge of the respective lateral portion of said one of said front and rear sections and (ii) a longitudinal edge of the connector sheet located on the inner surface of the other of said front and rear sections is directly contactable with the wearer, in use.

15. The wearing article as defined by claim 14, wherein each said connector sheet and the respective lateral portion of said one of said front and rear sections are folded outwardly along a folding line extending in the longitudinal direction of the tearable lines from the waist-hole to the associated leg-hole.

16. A disposable pull-on wearing article, comprising:

a pair of connector sheets;

a front section and a rear section having respective transversely opposite lateral portions connected together by said connector sheets to form a waist-hole, each of said front and rear sections having opposite inner and outer surfaces wherein the inner surface is directly contactable with a wearer, in use;

a crotch section connecting the front and rear sections and cooperating with said front and rear sections to form a pair of leg-holes;

said connector sheets defining tearable lines extending longitudinally from said waist-hole to said leg-holes so that the front and rear sections can be torn apart;

each of said connector sheets comprising joint zones permanently, directly joined to the respective transversely lateral portions of said front and rear sections, and between said joint zones, a non-joint zone free of direct attachment to said front and rear sections and defining one of said tearable lines;

wherein a tensile strength of said non-joint zones is at least 8N/25 mm width in a circumferential direction of the waist-hole, and a tear strength of said non-joint zones is in a range of 0.1 to 12N in a longitudinal direction of the tearable lines, and is lower than those of said transversely opposite lateral portions of said front and rear sections so that said tearable lines are reliably defined by the non-joint zones;

each said connector sheet has opposite inner and outer surfaces, the inner surface having a portion directly contactable with the wearer, in use, wherein each said connector sheet has the inner surface directly attached to the outer surfaces of both said front and rear sections, wherein an entire portion of the inner surface of said connector sheet between longitudinal edges of the respective lateral portions of said front and rear sections is directly contactable with the wearer, in use.

17. The wearing article as defined by claim 13, wherein an entire portion of the inner surface of said connector sheet between (i) the folding line and (ii) a longitudinal edge of the connector sheet located on the inner surface of said one of said front and rear sections is directly contactable with the wearer, in use.

18. The wearing article as defined by claim 17, wherein the inner and outer sections of each said connector sheet are bonded together to maintain the folded state of the connector sheet.

* * * * *